(12) United States Patent
Campbell

(10) Patent No.: US 6,440,665 B1
(45) Date of Patent: Aug. 27, 2002

(54) MODIFIED BIOLUMINESCENT PROTEINS AND THEIR USE

(75) Inventor: Anthony Keith Campbell, Penarth (GB)

(73) Assignee: University of Wales College of Medicine, Cardiff (GB)

( * ) Notice: Subject to any disclaimer, the term of this patent is extended or adjusted under 35 U.S.C. 154(b) by 0 days.

(21) Appl. No.: 09/225,302

(22) Filed: Jan. 5, 1999

Related U.S. Application Data

(62) Division of application No. 08/957,135, filed on Oct. 24, 1997, which is a division of application No. 08/270,314, filed on Jul. 5, 1994, now Pat. No. 5,683,888, which is a continuation of application No. 07/820,867, filed on Jan. 22, 1992, now abandoned, which is a continuation of application No. PCT/GB90/01131, filed on Jul. 23, 1990.

(30) Foreign Application Priority Data

Jul. 22, 1989 (GB) .............................................. 8916806

(51) Int. Cl.$^7$ ................................................ C12Q 1/68

(52) U.S. Cl. ............................................... 435/6; 435/8

(58) Field of Search .......................... 435/8, 6, 7.2, 7.1, 435/7.21

(56) References Cited

U.S. PATENT DOCUMENTS 5,683,888 A   11/1997   Campbell ....................... 435/8

FOREIGN PATENT DOCUMENTS

| EP | 0070685 | 1/1983 |
| EP | 0 103 469 | 3/1984 |
| EP | 0 137 515 | 4/1985 |
| EP | 0 302 381 | 2/1989 |

OTHER PUBLICATIONS

F. Tsuji et al., "Site–Specific Mutagenesis of the Calcium–Binding Photoprotein Aequorin", Proc. Natl. Sci., USA, vol. 83, Nov. 1986, pp. 8107–8111.
K. Kurose et al., Bioluminescene of the Ca$^{2+}$—Binding Photoprotein Aequorin After Cysteine Modification, Proc. Natl. Acad. Sci., USA, vol. 86, Jan. 1989, pp. 80–84.
S.C. Alter et al., "The Sulfhydryls of Firefly Luciferase Are Not Essential for Activity", Biochemistry, vol. 25, Nov. 7, 1986, pp. 1599–1605.
T. Cline et al., "Mutated Luciferases with Altered Bioluminescence Emission Spectra", The Journal of Biological Chemistry, vol. 249, Jul. 25, pp. 4668–4669.
E.A. Meighen et al., "Hybridization of Bacterial Luciferase with a Variant Produced by Chemical Modification", Biochemistry, 1971, Chemical Abstract No. 1279d.
W.H.R. Langridge et al., "Use of Low Light Image Microscopy to Monitor Genetically Engineered Bacterial Luciferase Gene Expression in Living Cells and Gene Activation Throughout the Development of a Transgenic Organism", New Methods in Microscopy and Low Light Imaging, 1989, SPIE vol. 1161, pp. 216–219.
T. Jenkins, "Measurement of Protein Phosphorylation by Covalent Modification of Firefly Luciferase", Coll. Med., Univ. Biochem. Soc. Trans., vol. 113, 1990, p. 315 (Chemical Abstract).
K. Wood et al., "Complementary DNA Coding Click Beetle Luciferase Can Elicit Bioluminescense of Different Colors", Science, May 12, 1989, vol. 244, pp. 700–702.
B. Li et al., "Creation of phosphorylation sites in proteins: Construction of a phosphorylatable human interfection α", Proc. Natl. Acad. Sci. USA, vol. 86, Jan. 1989, Cell Biology, pp. 558–562.
G. Sala–Newby et al., "Removal of Twelve C–Terminal Amino Acids from Firefly Luciferase Abolishes Activity", Biochemical and Biophysical Research Communications, Oct. 30, 1990, vol. 172, No. 2, pp. 477–482.
S. Zenno et al., "Bioluminescent Immunoassay Using a Fusion Protein of Protein A and the Photoprotein Aequorin", Biochemical and Biophysical Research Communications, Aug. 31, 1990, vol. 171, No. 1, pp. 169–174.
J. Casadei et al., "Expression and secretion of aequorin as a chimeric antibody by means of a mammlian expression vector", Proc. Natl. Acad. Sci. USA, vol. 87, Mar. 1990. pp. 2047–2051.
E. Kobatake et al., "Bioluminescent Immunoassay with a Protein A–Luciferase Fusion Protein", Analytical Biochemistry, vol. 208, 1993, pp. 300–305.
N. Watkins et al., "Requirement of the C–Terminal Proline Residue for Stability of the Ca$^{2+}$ Activated Photoprotein Aequorin", Biochem. J., 1993, vol. 293, pp. 181–185.
G. Sala–Newby et al., "Engineering a Bioluminescent Indicator for Cyclic AMP–Dependent Protein Kinase", Biochem. J., 1991, vol. 279, pp. 727–732.
G. Sala–Newby et al., "Engineering firefly luciferase as an indicator of cyclic AMP–dependent protein kinase in living cells", FEBS, vol. 307, No. 2, Jul. 1992, pp. 241–244.
Kemple et al., "Electron paramagnetic resonance of spin–labeled aequorin", XP–002162812, Chemical Abstract, vol. 101, No. 13, 1984.
Jenkins et al., "Measurement of protein phosphorylation by covalent modification of firefly luciferase", XP–002162811, Chemical Abstract, vol. 113, No. 3, 1990.

*Primary Examiner*—Lisa B. Arthur
(74) *Attorney, Agent, or Firm*—Young & Thompson

(57) ABSTRACT

A modified bioluminescent protein responds to different physical, chemical, biochemical or biological conditions to product light or radiation of altered characteristics when the bioluminescent reaction is initiated. The modified bioluminescent protein may respond to modification thereof, e.g. by covalent modification. The protein may include signal peptides to "target" it. DNA coding for the bioluminescent protein may be altered to include tissue specific promoter or enhancer genes so that the altered DNA acts as reporter gene.

1 Claim, 1 Drawing Sheet

FIG. 1

SEQUENCE LISTING

<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Leu Ser Arg Leu Ser Leu Arg Leu Leu Ser Arg Tyr Leu Leu
 1               5                  10                  15

```
<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Ser Ala Leu Leu Ala Leu Met Tyr Val Cys Pro Gly Lys Ala
 1               5                  10                  15

Asp Lys Glu

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Asp Glu Leu
 1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Arg Ala Ser Leu Gly
 1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Thr Lys Arg Ser Gly Ser Val Tyr Glu Pro Leu Lys Thr
 1               5                  10

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 6
cacctaatac gactcactat agggagaatg gaagacgcca aaaac          45

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 7
```
agaactgcct gccgcagatt ctcgca                                      26

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 8
atgctgtccc ggctgtccct gcggctgctg tcccggtacc tgctgaagac gccaaaaac    59

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 9
cacctaatac gactcactat agggagaatg ctgtcccggc tgtcc                  45

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
tctcgctgaa tacagttac                                               19

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
ccccaagctt agatctctct gatttttctt gcgt                              34

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
tgcgagaatc tgcggcaggc agttct                                       26

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (3)
<223> OTHER INFORMATION: Variable amino acid

<400> SEQUENCE: 13

Arg Arg Xaa Ser
 1

```
<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Thr Lys Arg Ser Gly Ser Val Tyr Glu Pro Leu Lys Ile
  1               5                  10

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 15
taatacgact cactataggg gagagaatgg tcaagcttta catcagactt cgac        54

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 16
gaattcttag gggacagctc caccgta                                      27

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gctcgtctta ttgaagataa tgaatatact gctcgttttg gt                     42
```

MODIFIED BIOLUMINESCENT PROTEINS AND THEIR USE

CROSS REFERENCE TO RELATED APPLICATIONS

This application is a division of copending application Ser. No. 08/957,135, filed Oct. 24, 1997, which is a division of Ser. No. 08/270,134, filed Jul. 5, 1994, now U.S. Pat. No. 5,683,888, which is a file wrapper continuation of Ser. No. 07/820,867, filed Jan. 22, 1992 now abandoned, which is a continuation of PCT/GB90/01131, filed Jul. 23, 1990.

This invention relates to bioluminescent proteins, in particular it relates to bioluminescent proteins which have been modified, for example by chemical means or by genetic engineering. Such modified bioluminescent proteins, hereinafter referred to as "rainbow proteins", may be used in the detection and quantification of cells, microbes such as bacteria, viruses and protozoa, and substances of biological interest such as substrates, metabolites, intra- and extracellular signals, enzymes, antigens, antibodies and nucleic acids.

Bioluminescence is the oxidation of an organic molecule, the "luciferin", by oxygen or one of its metabolites, to emit light. The reaction is catalysed by a protein, usually known as a "luciferase", or a "photoprotein" when the luciferin is so tightly or covalently bound to the luciferase that it does not diffuse off into the surrounding fluid.

$O_2$+lucifern+luciferase→oxyluciferin+light (or $O_2^-$ or $H_2O_2$) (or photoprotein) to three other substances may also be required to be present in order to generate light, or to alter its colour, and they are as follows:

(a) A cation such as $H^+$, $Ca^{2+}$, $Mg^{2+}$, or a transition metal such as $Cu^+/Cu^{2+}$, $Fe^{2+}/Fe^{3+}$.
(b) A cofactor such as NADH, FMU, or ATP.
(c) A fluor as an energy transfer acceptor.

Figure 1:
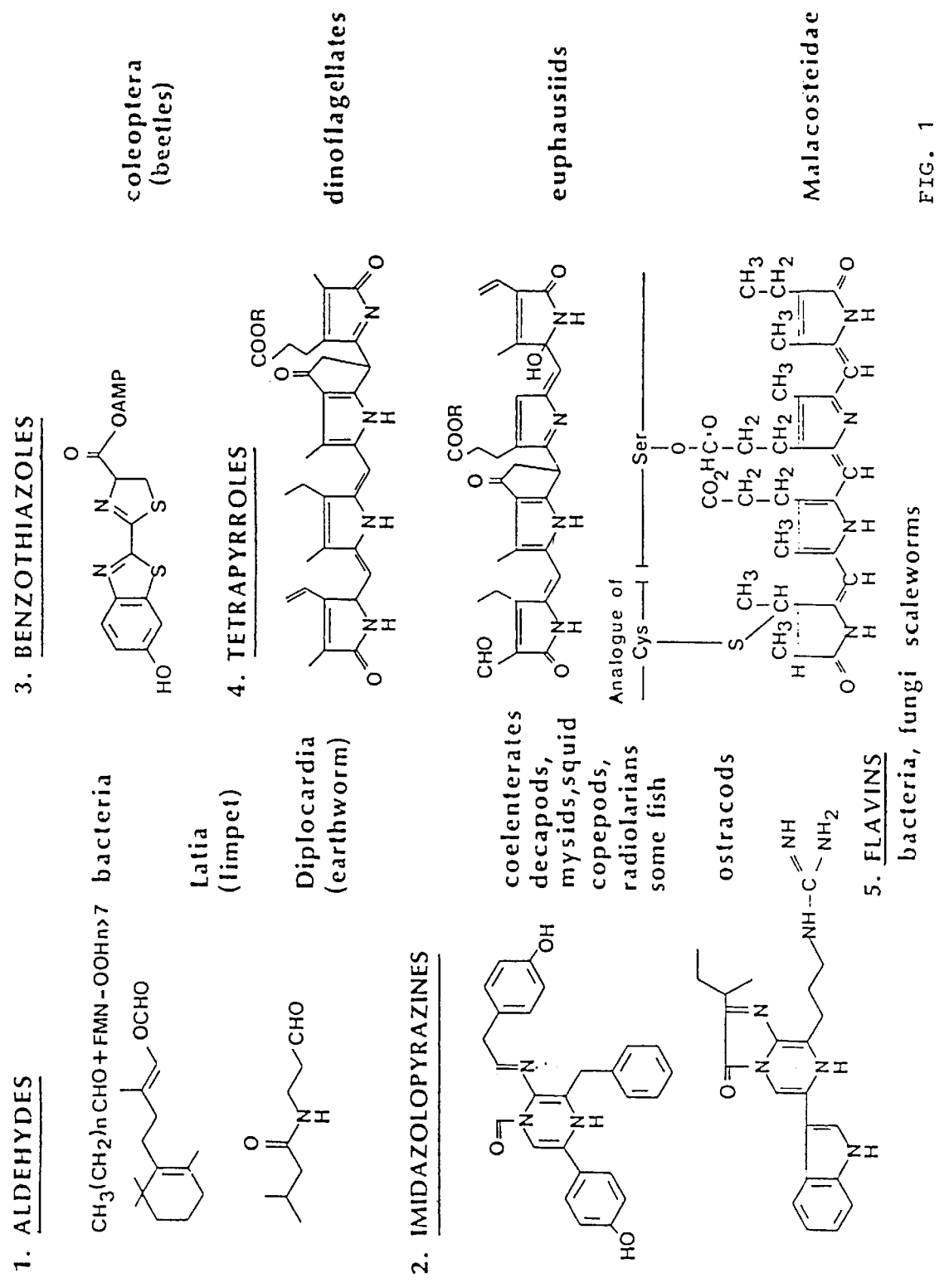

Five chemical families of luciferin have been identified so far (see FIG. 1 of the attached drawing):

(a) Aldehydes (found in bacteria, freshwater limpet *Latia* and earthworms).
(b) Imidazolopyrazines (found in Sarcomastigophora, Cnidaria, Ctenophora, some Arthropoda, some Mollusca, some Chordata).
(c) Benzothiazole (found in beetles such as fireflies and glowworms).
(d) Linear tetrapyrroles (found in dinoflagellates, euphasiid shrimp, some fish).
(e) Flavins (found in bacteria, fungi, polychaete worms and some molluscs).

Reactions involving these luciferins may result in the emission of violet, blue, blue-green, green, yellow or red light and occasionally UV or IR light and such emission may or may not be linearly or circularly polarised. Reference is directed to Chemiluminescence principles and applications in biology and medicine, A. K. Campbell, publ. 1988 Horwood/VCH Chichester Weinheim, for further discussion of bioluminescent reactions.

It has now been found that the light emitted from a bioluminescent reaction involving a modified bioluminescent or "rainbow" protein, may be changed in intensity, colour or polarisation. Such a change can then be used in various assays for detecting, locating and measuring cells, microbes and biological molecules.

In this instance, the cell or substance causes a physical or chemical change, such as phosphorylation, to a rainbow protein such as a genetically engineered luciferase, resulting in a change in intensity, colour or polarisation of the light emission. The bioluminescent reaction is triggered by adding, for example, the luciferin, and modification of the luciferase by the cell or substance being measured causes the reaction to emit light at a shorter or longer wavelength. This enables specific reactions to be detected and quantified in live cells, and within organelles or on the inner or outer surface of the plasma membrane, without the need to break them open, and without the need for separation of bound and unbound fractions.

According to one aspect of the invention there is provided a bioluminescent protein capable of taking part in a bioluminescent reaction to produce light or radiation of altered characteristics under different physical, chemical, biochemical or biological conditions.

The rainbow protein may be produced by the alteration, substitution, addition or removal of one or more amino acids from the end of or within the luciferase or photoprotein. As a result the light emission from the oxyluciferin may be of different colours or different states of polarisation depending on the physical or chemical conditions. A change in colour to another part of the rainbow spectrum may be induced by:

(a) A change in cation concentration such as H, Ca Mg; or transition metal.
(b) A change in anion concentration such as $Cl^-$ or phosphate.
(c) Covalent modification of the new protein by enzymes causing phospho- or dephosphorylation (including ser/thr, his, and tyr kinases and phosphatases) transglutamination, proteolysis, ADP ribosylation, gly-or glu-cosylation, halogenation, oxidation, methylation and myristilation.
(d) Binding to the rainbow protein of an antigen, an intracellular signal such as cyclic AMP, cyclic GMP, Ip3, Ip4, diacyl glycerol, ATP, ADP, AMP, GTP, any oxy or deoxyribonucloside or nucleotide, a substrate, a drug, a nucleic acid, a gene regulator protein.
(e) Expression of its nucleic acid inside a live cell, as well as its modification or regulation within the cell by gene expression such as promoters, enhancers or oncogenes.

Single or multiple mutations and deletions may be detected in a piece of DNA (eg a PCR product) by linking the "rainbow protein" to one end of the DNA and an energy transfer acceptor or quencher to the other end. Muclease attack at the mutation will separate the rainbow protein from the acceptor or quencher and thus cause a change in intensity, colour or polarisation of the light emission.

Such alteration, substitution, addition or removal of one or more amino acids may be achieved by chemical means. Alteration of an acid includes alkylation (eg. methylation), phosphorylation and various other covalent modifications of the type outlined herein. Alternatively the nucleic acid coding for the luciferase or photoprotein may be altered by modifying, substituting, inserting or deleting one or more nucleotides such that the resulting protein has gained or lost a site which interacts with the cations, anions, intracellular signal, covalent modification; proteins or nucleic acid to be measured. The insertion or deletion of nucleotides is normally produced by site directed mutagenesis or by opening up the gene with a specific restriction enzyme, inserting or deleting a selected nucleotide sequence and then sealing up of the gene again or using specific primers with the polymerase chain reaction. The nucleic acid is then transcribed to mRNA and this is then translated to form the rainbow protein either inside a bacterial or eukaryotic cell, or in vitro using, for example, rabbit reticulocyte lysate. The new nucleic acid may contain an RNA polymerase promoter such as T7, SP6, or mammalian promotors such as actin, myosin, myelin proteins, MMT-V SV40, antibody G6P dehydrogenase, and can be amplified in vitro using the polymerase chain reaction. The result is that the rainbow protein can be produced either in a live cell such as a cancer cell, or without cells using enzymatic reactions in vitro. The addition of tissue specific promoter or enhancer sequences to the 5' or 3' end of the DNA coding for the native or altered bioluminescent protein will enable it to be used as a reporter gene and to be expressed specifically in a particular cell or tissue, the expression being detectable by the appearance of a change in light intensity, colour or polarisation.

Another way of producing the DNA for a rainbow protein is to separate into two halves the original DNA for the bioluminescent protein. A piece of DNA or gene is then inserted between the two halves by ligating one half to the 5' end and the other to the 3' end. Alternatively the rainbow protein DNA could be generated using the polymerase chain reaction so that the sense primer had one part of the rainbow protein DNA linked at 5' end and the antisense primer and the other part linked at the 3' end (i.e. antisense). The pieces of DNA or gene of interest, in the middle, could be from two separate genes. For example one could code for an energy transfer protein, the other for a bioluminescent protein. Only when the two are linked together via a peptide (from DNA/RNA) will the rainbow protein be generated and a shift in colour occur. The energy transfer protein could be any fluor bound covalently or non-covalently to the protein, for example the green fluorescent protein from Aequorea, Obelia, Penilla or other cnidarians, or the blue or yellow fluorescent protein from luminous bacteria, or a flavoprotein, or a phyobiliprotein. The whole protein or just the fluorescent demain may be used. The bioluminescent protein would be any luciferase for example bacterial, firefly, glowworm or copepod, or any photoprotein for example aequorin, obelin or a radiolarin such as thalassicollin.

The protein or its DNA or RNA may be incorporated into a live bacterium or eukaryotic cell by using a virus, plasmid, calcium phosphate transfection, electroporation, liposome fusion or membrane pore forming proteins. Once inside, only live cells with the appropriate biochemistry will produce the "rainbow effect". By incorporating the "rainbow protein" gene into an embryo, oocyte, sperm, seed or seedling a transgenic animal or plant may be produced, enabling gene expression, cell regulation, drug action, or cell damage to be located and measured in individual organs using the "rainbow effect". These new organisms may also be used in home aquaria, on aeroplane runways, as safe lights at sea, and as house plants.

The rainbow protein may also be incorporated in a different part of the cell by chemical means or genetically engineering the protein to contain a signal peptide which locates it to the inner or outer surface of the plasma membrane or within a particular intracellular organelle (e.g. peroxisome, mitochondrion, chloroplast, endoplasmic reticulum, golgi, secretory vesicle, nucleus or endosme.

Addition of a signal peptide, either chemically or by genetic engineering, will enable the normal or altered luciferase or photoprotein to be targeted into a specific organelle within the cell, or onto the inner or outer surface of the plasma membrane. For example the sequence MLSRLSLRLLSRYLL (SEQ ID NO: 1) at the N terminus will locate the bioluminescent protein in the mitochondria, and KKSALLALMYVCPGKADKE (SEQ ID NO: 2) on the N terminus will target the protein to the endoplasmic reticulum, a KDEL (SEQ ID NO: 3) sequence at the C terminus retaining it there.

The initial luciferase or photoprotein or its gene may come from any of the known chemistries in bioluminescence (see FIG. 1) or from the wide range of uncharacterised luminous organisms from more than 700 genera representing at least 16 phyla. The luciferin may be synthesised chemically and added to the biological reaction or cell to generate light. Aternatively, the gene coding for the enzymes responsible for making the luciferin may be linked to the "rainbow protein" gene so that the artificial operon or fusion gene expresses both rainbow protein and makes luciferin in the live cell from normal cell constituents such as amino acids.

According to a second aspect of the invention there is provided a method of producing a bioluminescent protein by altering, substituting, adding or deleting one or more amino acids to the protein by chemical means or by genetically engineering the nucleic acid coding for the protein.

According to a further aspect of the invention there is provided nucleic acid coding for the bioluminescent protein as hereinbefore defined.

The rainbow protein, or the nucleic acid coding for it, may be used in a range of biological investigations; such as:
(a) Detection, location and measurement of microbes (protozoa, bacteria, viruses).
(b) Detection and location of cancer cells.
(c) Measurement of enzymes, intracellular signalling and other turnover reactions in cells or fluids.
(d) DNA and RNA binding assays.
(e) Immunoassay and other protein binding assays.

The rainbow proteins and their parent nucleic acids also may be used in genetic engineering, in the development of transgenic animals, plants and microbes, and in horticulture.

According to yet a further aspect of the invention there is provided the use of a rainbow protein, or the nucleic acid coding for the rainbow protein, for the detection, location or measurement of substances of biological interest such as microbes, cells or biological molecules or reactions therein.

In this aspect, the reaction or substances of biological interest are made to interact with the rainbow protein or its parent nucleic acid. Such interactions include direct or indirect linking such as non-covalent or covalent binding as well as energy transfer processes.

Although the invention has been described above it is to be understood that it includes any inventive combination of the features set out above or in the following description.

The invention may be performed in various ways and will be further described with reference to the following examples:

EXAMPLE 1

Detection of Phosphorylation of a Rainbow Protein

The peptide leu arg arg ala ser leu gly (SEQ ID NO: 4), known as kemptide, or RTKRSGSVYEPLKT (SEQ ID NO: 5) know as malantide was covalently linked to firefly luciferase using disuccinyl suberate at pH8. Addition of 125 $\mu$l protein kinase A+cyclic AMP (200 $\mu$M)+125 $\mu$M ATP caused phosphorylation of the kemptide, now attached to the luciferase. The resulting shift in colour from yellow-green to red a pH 7.8 or from red or yellow-green at pH 6.5, measured as a ratio in a dual wavelength chemiluminometer, enabled the rate of protein phosphorylation by the kinase to be assayed, and dephosphorylation induce by phosphatase to be assayed subsequently by the reversal of the ratio.

EXAMPLE 2

Engineering Firefly Luciferase cDNA coding for firefly luciferase was amplified using the polymerase chain reaction (PCR) using 5' sense primers with a T7 RNA polymerase promoter, and 3' antisense primers as follows: Primer code in brackets 5' sense primers
(105) CACCTAATACGACTCACTATAGG-GAGAATGGAAGACGCCAAAAAC (SEQ ID NO: 6)
(107) AGAACTGCCTGCCGCAGATTCTCGCA (SEQ ID NO: 7)
(110) ATGCTGTCCCGGCTGTCCCTGCGGCT-GCTGTCCCGGTACCTGCTGAAGACGC CAAAAAC (SEQ ID NO: 8)
(111) CACCTAATACGACTCACTATAGG-GAGAATGCTGTCCCGGCTGTCC (SEQ ID NO: 9)

3' antisense primers
(100) TCTCGCTGAATACAGTTAC (SEQ ID NO: 10)
(106) CCCCAAGCTTAGATCTCTCT-GATTTTTCTTGCGT (SEQ ID NO: 11)
(108) TGCGAGAATCTGCGGCAGGCAGTTCT (SEQ ID NO: 12)

The following firefly luciferase cDNA's were constructed using primers in brackets:
(a) full length (105+100)
(b) 36 bp i.e. missing peroxisomal signal peptide (105+106)
(c) protein kinase A site (RRXS) (SEQ ID NO: 13) in middle of protein (step 1: 105+108 and 107+100; step 2:2 halves from step 1+105+100).
(d) mitochondrial signal at N terminus (step 1:110+100; step 2: step 1 sample +111+100).

The PCR reaction in 50 μl contained 10 mM Tris pH 8.3, 0.01% gelatin, 0.4 μTaq polymerase, 2 mM $MgCl_2$, 0.2 mM each dATP, dGTP, dTTP, dCTP, 0.5 μM of each primer, 1 μl DNA (ca 1–100 ng). The reaction, covered with 50 μl mineral oil, was incubated in a Perkin-Elmer thermal cycler for 25 cycles: 94° C. 1 minute, 55° C. 1 minute, 72° C. 2 minutes+5 seconds extension on each cycle, then for 30 minutes at 37° C. with 1 U E.coli DNA polymerase (Klenow fragment).

Successful PCR was confirmed by a band on agarose gel electrophoresis. The cDNA was purified by centricon to remove primers, and precipitated in 70% ethanol, 0.7 mM $NH_4$ acetate after extraction with buffered phenol: $CHCl_3$: secondary amyl alcohol (25:24:1). The DNA (0.5–1 μg dissolved in 10 mM Tris 0.1 or 1 mM EDTA pH 7.4–7.5) was transcribed in the T7 RNA polymerase in buffer containing 40 mM Tris, pH 7.4–7.5, 6 mM $MgCl_2$, 10 mM dithiothreitol, 0.1 mg/ml bovine serum albumin, 2 mM spermidine, 0.5 mM each ATP, CTP, UTP, 0.1 mM GTP, 0.5 mM cap m7 G (5') ppp (5') G, 1000 U RNAsin/ml, 800 U T7 RNA polymerase ±2 μC, $^{32}P$ UTP for up to 4 hours (1–2 hours optimal), at 37° C. The reaction was stopped in the ice cold phenol; $CHCl_3$: secondary amyl alcohol (25:24:1), and the RNA precipitated in 70% ethanol+0.7 M $NH_4Ac$, and stored at −20° C.

The RNA was centrifuged, redissolved in 20 μl 70 mM Tris, 1 mM EDTA pH 7.4–7.5 and 1 μl incubated with 5–10 μl rabbit reticulocyte lysate for 1 hour at 30° C. to synthesize the luciferase. Luciferase, after dilution, 1/1000 is assayed for light emission directly in 50 mM tris, 10 mM $MgAc_2$, 0.1 mg/ml bovine serum albumin, 0.1–0.2 mM luciferin, 0.5–mM ATP, pH 7.8, or isolated by isoelectric focusing. The mutant (RRXS) luciferase has a pI of ca 7.1or 6.8, and the normal luciferase pI ca 6.8. The luciferase with mitochondrial signal also separated from the normal luciferase. On addition of the rabbit reticulocyte lysate containing this altered luciferase it was taken up by added mitochondria, as shown by centrifugation and light emission from the mitochondria and luciferase.

Phosphorylation of the RRXS containing luciferase with protein kinase A, cyclic AMP (0.2 mM), ATP (0.1–1 mM) ph7, caused the luciferase to change its pI back towards 6.8, and to shift its colour. The RRXS luciferase had a greener light emission than the native luciferase detected using a dual wavelength chemiluminometer with interference filters (maximum transmission ca 545 and 603 mM).

Primers containing kemptide nucleotide sense or antisense sequence (LRRASLG) or malantide RTKRSGSVYE-PLKI (SEQ ID NO: 14) were also added either to N or C terminus using a one or two step PCR reaction. These also produced luciferase which could be phosphorylated thereby altering its intensity and colour.

EXAMPLE 3

Preparation of Engineered Aequorin cDNA or genomic coding for the $Ca^{2+}$-activated photoprotein was PCR'd in a similar way to that for firefly luciferase. Using one or two step PCP the protein kinase A recognition peptide kemptide (LRRLALG) or malantide (as Example 2) was added to the terminus. The mutant aequorin had different kinetic properties enabling protein kinase A to be detected by phosphorylating the altered aequorin (above).

Normal aequorin primers =5' sense TAATACGACTCAC-TATAGGGGAGAGAATGGTCAAGCTTTA-CATCAGACTTCGAC (SEQ ID NO: 15) and 3' antisense GAATTCTTAGGGGACAGCTCCACCGTA (SEQ ID NO: 16). For insertion of kemptide at the N terminus the nucleotide sequence equivalent to LRRASLG was attached to the first 15 bases (including ATG) of the 5' end of aequorin. In step 2, the T7 RNA polymerase promoter was added to form the kemptide-aequorin in vitro for in vitro phosphorylation. Genomic aequorin DAN (made by PCR) was at least as active as that made from mRNDA by reverse transcriptase PCR.

EXAMPLE 4

Detection of Cancer Cells in Blood

A blood sample (1 ml) is mixed with a suspension of liposomes containing mRNA coding for a rainbow protein catalysing the benzothiazole reaction c in FIG. 1.

This mRNA was produced as follows:

The gene coding for firefly luciferase was first isolated from a cDNA library in E. coli using pCDV1 plasmid primer+Honjo linker containing SP6 RNA polymerase promoter. A nucleotide sequence GCTCGTCTTATTGAA-GATAATGAATATACTGCTCGTTTTGGT (SEQ ID NO: 17) representing the phosphorylation site for tyrosine kinase activity of the myc onocogene was inserted at the EcoRI restriction site 30 base pairs downstream from the ATG at the 5' end. The DNA was resealed, recloned and the plasmid insert transcribed by SP6 RNA polymerase in vitro to produce mRNA for the rainbow protein. The original protein produced yellow-green light but the rainbow protein when phosphorylated in the cell produces red light. Thus the presence of cancer cells was detected in blood sample from a leukaemia patient by measuring the ratio of yellow-green (545 nm) to red (603 nm) light in a dual wavelength chemiluminometer.

EXAMPLE 5

Detection of Salmonella

The cDNA for the rainbow protein in Example 4 containing SP6 RNA polymerase promoter was inserted into *Salmonella* phage. Addition of this phage to *Salmonella* resulted in expression of the rainbow protein and the generation of red light, enabling as few as 1 bacterium per 20 ml to be detected.

EXAMPLE 6

Detection of HIV RNA

A sample (1 ml) of blood from a patient with AIDS was extracted with 4 M guanidium isothiocyanate and the nucleic acid precipitated with ethanol/HH acetate. An oligonucleotide (10 μl, 1 μM) labelled with a rainbow protein generated from the photoprotein obelin was added to 100 μl redissolved RNA at 50° C. and the mixture cooled for 10 minutes at 0° C. The oligonucleotide was specific for a sequence in the HIV coat protein. Binding this to HIV RNA resulted in a shift in the light emission from the rainbow protein from light blue (475 nm) to blue (440 nm). This was detected as a shift in the ratio of light emission at these two wavelengths in a dual photomultiplier chemiluminometer.

EXAMPLE 7

Measurement of Testosterone in Blood

Testosterone carboxyoxime is reacted with the rainbow protein from the photoprotein obelin to form a testosterone rainbow protein conjugate. 5 μl of this containing 1 nmol was incubated with a solution of antibody labelled with fluorescein to testosterone (50 μl) pH 7.4 for 30 minutes in the presence or absence of varying concentrated of standard testosterone. The bioluminescent reaction was triggered by addition of Ca and the ratio of light at 475 nm to 530 nm measured. Increasing the concentration of standard testosterone increased the ratio at 475/530. This procedure could be carried out without the need to separate bound from free antigen.

EXAMPLE 8

Detection of Listeria

A sample of suspect food is boiled to extract DNA. A sense primer to the specific *Listeria* gene or domain covalently coupled to obelin cDNA+5P6 RNA polymerase promotor and antisense primer covalently coupled to antisense green fluorescent protein (GFP) cDNA is used to amplify the *Listeria* gene using the polymerase chain reaction. The result is DNA coding for a new rainbow protein and transcribable by SP6 RNA polymerase.

This DNA is transcribed and the mRNA translated using rabbit reticulocyte lysate. Coelenterazine is added to reactivate obelin. The ratio of light at 510/475 nm for rainbow protein versus obelin alone is directly proportional to the amount of *Listeria* DNA originally present in the food sample. When no *Listeria* are present the ratio of ratios is 1.

EXAMPLE 9

Measurement of Nucleic Acid Hybridisation by Polarisation

The reaction described in Example 6 was carried out but the light emission was detected in a dual photomultiplier chemiluminometer containing two plane polarised filters with the polarisation planes at 90° to each other. The ratio between the two photomultipliers was related to the amount of HIV RNA present.

EXAMPLE 10

Measurement of Cyclic AMP or Ip3

Using a two step PCR reaction as described in Examples 2 and 3, the cyclic AMP binding domain from the bacterial CAP protein or the Ip3 binding domain of the endoplasmic reticulum receptor was added to the or C terminus or into firefly luciferase or aequorin. The altered proteins were made in vitro from the PCR DNA product as described in Examples 2 and 3, and characterised by activity and colour of light emission cyclic AMP or Ip3. A change in both intensity and colour enabled CAMP or Ip3 to be measured in cell extracts to in living cells. Using an image intensifier a CAMP or Ip3 "cloud" could be visualised in this one cell. Similarly the aequorin or luciferase could be seen within the ER or a mitochondrion if it was first made with an EP or mitochondrial signal attached to it (±KDEL) at the C terminus.

It will be appreciated that the bioluminescent protein may be synthesised from amino acid sequences or using DNA or RNA synthesis techniques, instead of by modification of a protein produced by an organism.

---

What is claimed is:

1. A method of monitoring the interaction between a substrate and a substance to which said substrate is exposed, which comprises:

coupling a bioluminescent protein portion, capable of taking part in a bioluminescent reaction, to a first portion of said substrate, coupling an energy transfer protein portion to a second portion of the substrate, whereby said bioluminescent protein portion and said energy transfer protein portion are in an energy transfer relationship, exposing said substrate to said substance, initiating said bioluminescent reaction, and monitoring at least one of the amount of light emitted directly by said bioluminescent protein portion and the amount of light emitted by said energy transfer protein portion resulting from energy transfer between said bioluminescent protein portion and said energy transfer protein portion, wherein said substrate comprises a nucleic acid fragment containing one or more mutations or deletions and said substance comprises a nuclease responsive to said one or more mutations or deletions to cleave said nucleic acid fragment.

* * * * *